US006776996B2

(12) United States Patent
Sun et al.

(10) Patent No.: US 6,776,996 B2
(45) Date of Patent: Aug. 17, 2004

(54) PESTICIDAL MATRICES

(75) Inventors: Guanglin Sun, Plainsboro, NJ (US); Fakhruddin Ahmed, Princeton Junction, NJ (US); Bruce Christian Black, Yardley, PA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/094,279

(22) Filed: Jun. 9, 1998

(65) Prior Publication Data

US 2003/0194419 A1 Oct. 16, 2003

Related U.S. Application Data

(60) Provisional application No. 60/052,071, filed on Jul. 9, 1997.

(51) Int. Cl.$^7$ ................................................ A01N 25/28

(52) U.S. Cl. ....................... 424/417; 424/405; 424/408; 424/409; 424/487; 424/489; 424/497; 424/93.1; 424/93.2; 424/93.6

(58) Field of Search ................................ 424/405, 407, 424/408, 409, 417, 419, 487, 93.1, 93.2, 93.6, 435, 330.1, 489, 497, 78.01, 78.09, 78.31; 504/116

(56) References Cited

U.S. PATENT DOCUMENTS

| | | | | |
|---|---|---|---|---|
| 3,541,203 | A | 11/1970 | Fogle et al. | 424/17 |
| 4,244,836 | A | 1/1981 | Frensch et al. | 252/316 |
| 4,948,586 | A | 8/1990 | Bohm et al. | 424/406 |
| 5,560,909 | A | * 10/1996 | Rheaume et al. | 424/93.1 |
| 6,001,382 | A | 12/1999 | Levy | 424/405 |

FOREIGN PATENT DOCUMENTS

| | | | |
|---|---|---|---|
| EP | 014514 | B1 | 6/1986 |
| EP | 250908 | A2 | 1/1988 |
| EP | 0 697 170 | A1 | 2/1996 |
| WO | WO 89/04170 | | 5/1989 |

* cited by examiner

*Primary Examiner*—Neil S. Levy
(74) *Attorney, Agent, or Firm*—Keil & Weinkauf

(57) ABSTRACT

The present invention provides improved coated pesticidal matrices and a process for their preparation. The present invention also provides a wettable powder pesticidal composition containing the improved coated pesticidal matrices.

58 Claims, No Drawings

PESTICIDAL MATRICES

This application claims priority from copending provisional application(s) serial number 60/052,071 filed on Jul. 9, 1997.

BACKGROUND OF THE INVENTION

Certain pesticidal agents are inactivated by ultra-violet radiation from the sun. Because those pesticidal agents are useful for the control of pests and are applied in areas where they will be exposed to ultraviolet radiation, there is a need for photostable compositions containing those agents.

To prevent ultraviolet inactivation of pesticidal agents, compositions have been prepared which contain ultraviolet absorbers and/or reflectors and a pesticidal agent.

U.S. Pat. No. 3,541,203 describes a protected virus composition for insect control. The preferred composition includes a virus, an actinic light absorbing material and a polymeric binder material. However, the process used to prepare the preferred compositions of U.S. Pat. No. 3,541,203 requires the use of toxic materials and numerous washing steps with flammable solvents thus making it unsuitable for commercial manufacture.

U.S. Pat. No. 4,948,586 discloses a microencapsulated insecticidal pathogen. Four microencapsulated compositions are shown to decrease the photoinactivation of *Autographa californica* NPV. However, the microencapsulated compositions retain only from 30.7 to 71.43% of the original activity upon exposure to sunlight. U.S. Pat. No. 4,948,586 discloses a method of preparing microencapsulated insecticidal pathogens which has numerous steps and is both time-consuming and laborious. It is apparent that neither the process, nor the microencapsulated insecticidal pathogens, described in U.S. Pat. No. 4,948,586, are entirely satisfactory for providing a product stable to ultraviolet radiation.

U.S. Pat. No. 5,560,909 discloses a process for the preparation of insecticidal compositions which requires the modification of the charge of a charged polymer to precipitate the polymer and entrap the insecticide. However, this process is not entirely satisfactory because a small amount of the functional groups on the polymer will remain charged in the final product, resulting in a less efficacious product.

EP 697170-A1 discloses a process for the preparation of coated pesticidal agents which requires that the coating polymer be completely dissolved and which adjusts the pH of the coating solution to attain such dissolution. Unfortunately, such dissolution reduces some of the desirable properties of the coating polymer, resulting in a less efficacious product.

SUMMARY OF THE INVENTION

The present invention comprises an improved process for the preparation of a coated pesticidal matrix, which process comprises: a) preparing an aqueous mixture comprising a pesticidal agent, a pH-dependent polymer and water, wherein the pH is below the solubilization pH of the polymer; and b) drying the aqueous mixture to produce the coated pesticidal matrix. The aqueous mixture optionally includes a plasticizer, an ultraviolet protector, an activity enhancer and/or a glidant thus resulting in their presence in the coated pesticidal matrix. Preferably, the pesticidal agent is a particulate chemical insecticide or a viral, bacterial or fungal insecticidal pathogen.

The present invention also comprises wettable powder pesticidal compositions which comprise coated pesticidal matrices, together with suitable carriers.

The present invention further comprises a method for improving the residual control of a pest comprising the application of a matrix made by the process of this invention.

It is an object of the present invention to provide a coated pesticidal matrix which retains the desirable properties of the coating polymer and thus retains a significant amount of its original pesticidal activity after exposure to ultra-violet radiation.

It is also an object of the present invention to provide an improved process for the preparation of a coated pesticidal matrix under mild conditions which avoid degradation of the pesticidal agent.

Other objects of this invention will be apparent to those skilled in the art from the following description and the appended claims.

DETAILED DESCRIPTION OF THE INVENTION

The improved process of this invention comprises:

a) preparing an aqueous mixture comprising a pesticidal agent, a pH-dependent polymer, optionally a plasticizer, optionally an ultraviolet protector, optionally an activity enhancer, optionally a glidant, and water, provided that the pH of the aqueous mixture is below the solubilization pH of the pH-dependent polymer; and b) drying the aqueous mixture of step (a) to produce a coated pesticidal matrix.

Advantageously, it has been found that coated pesticidal matrices, prepared from a pH-dependent polymer without converting a substantial number of free carboxylic acid groups in the polymer to their salt form, retain a high percentage of their original activity after exposure to ultraviolet radiation and have greater residual activity compared to coated pesticidal agents prepared by the coating process described in EP 697170-A1. The instant process accomplishes this by providing an aqueous mixture wherein the pH is below the solubilization pH of the pH-dependent polymer.

In a preferred embodiment of the present invention, coated pesticidal matrices prepared by the process of this invention comprise about 1 to 50% by weight of a pesticidal agent, about 5 to 50% by weight of a pH-dependent polymer, 0 to about 25% by weight of a plasticizer, 0 to about 30% by weight of an ultraviolet protector, 0 to about 75% by weight of an activity enhancer, and 0 to about 15% by weight of a glidant.

More preferred coated pesticidal matrices prepared by the process of this invention are those comprising about 5 to 35% by weight of a pesticidal agent, about 10 to 45% by weight of a pH-dependent polymer, 0 to about 25% by weight of a plasticizer, 0 to about 20% by weight of an ultraviolet protector, 0 to about 45% by weight of an activity enhancer, and 0 to about 10% by weight of a glidant.

The aqueous mixture of this invention may be dried using any conventional drying technique which allows the pH-dependent polymer to form a coating film on the outside, and a binding film inside, of the matrix particles. Preferably, the aqueous mixture is spray dried or air dried. The coated pesticidal matrices of the present invention preferably have a particle size less than about 20 μm, and, more preferably, have a particle size of about 2 μm to 10 μm.

Pesticidal agents suitable for use in the present invention include chemical and biological insecticides, acaricides, nematicides, fungicides, herbicides, and the like, and mixtures thereof. In particular, pesticidal agents which are subject to inactivation of their desired activity by ultraviolet radiation are preferred pesticidal agents for use in this invention.

Chemical insecticides include, but are not limited to, arylpyrroles such as chlorfenapyr; amidinohydrazones such as hydramethylnon; hydrazinecarboxyamides such as those described in U.S. Pat. No. 5,543,573; 1,4-diaryl-2-fluoro-2-butenes such as those described in EP 811593-A1, including 1-[1-(p-chlorophenyl)-2-fluoro-4-(4-fluoro-3-phenoxyphenyl)-2-butenyl]cyclopropane, (R,S)-(Z)-; 1-substituted-2-(nitromethylene)imidazolidines such as imidacloprid and 1-(6-chloro-3-pyridyl)-2-(nitro-methylene) imidazolidine; phenylpyrazoles such as fipronil; and the like, and mixtures thereof. The chemical insecticides of this invention, when in solid form, preferably have a particle size prior to coating of less than about 10 μm and, more preferably, have a particle size of about 0.1 μm to 5 μm.

Biological insecticides include all naturally occuring and genetically modified varieties of insect biological control agents such as viral pathogens, bacterial pathogens, and fungal pathogens. Viral pathogens suitable for use include DNA viruses, RNA viruses and unclassified insect viruses such as gonad-specific virus (GSV).

The DNA viruses include double stranded enveloped DNA viruses such as (Subfamily, then species) Entomopoxvirinae (*Melolontha melolontha* entomopoxvirus), and Eubaculovirinae (*Autographa californica* MNPV; *Heliocoverpa zea* NPV; *Trichoplusia ni* GV), as well as double stranded nonenveloped DNA viruses such as Iridoviridae (Chilo iridescent virus) and single stranded nonenveloped DNA viruses such as Parvoviridae (Galleria densovirus).

The RNA viruses include double stranded enveloped RNA viruses such as Togaviridae (Sindbis virus), Bunyaviridae (Beet leafcurl virus) and Flaviviridae (Wesselbron virus), as well as double stranded nonenveloped RNA viruses such as Reoviridae (Corriparta virus) and Birnaviridae (Drosophila X virus), as well as single stranded nonenveloped RNA viruses such as Picornaviridae (Cricket paralysis virus), Tetraviridae (*Heliothis armigera* stunt virus) and Nodaviridae (Black beetle virus).

The Subfamily of double stranded DNA viruses Eubaculovirinae includes two genera, nuclear polyhedrosis viruses (NPVs) and granulosis viruses (GVs), which are particularly useful for biological control because they produce occlusion bodies in their life cycle. Examples of NPVs include *Lyinantria dispar* NPV (gypsy moth NPV); *Autographa californica* NPVs such as V8vEGTDEL, V8vEGTDEL-AaIT, AcMNPV E2, AcMNPV L1, AcMNPV V8, and AcMNPV Px1; *Anagrapha falcifera* NPV (celery looper NPV); *Spodoptera littoralis* NPV; *Spodoptera frugiperda* NPV; *Heliothis armigera* NPV; *Mamestra brassicae* NPV; *Choristoneura fumiferana* NPV; *Trichoplusia ni* NPV; *Heliocoverpa zea* NPV; and *Rachiplusia ou* NPV; and the like. Examples of GVs include *Cydia pomonella* GV (coddling moth GV), *Pieris brassicae* GV, *Trichoplusia ni* GV, *Artogeia rapae* GV, *Plodia interpunctella* GV (Indian meal moth), and the like. Examples of entomopox viruses (EPVS) include *Melolontha melolontha* EPV, *Amsacta moorei* EPV, *Locusta migratoria* EPV, *Melanoplus sanguinipes* EPV, *Schistocerca gregaria* EPV, *Aedes aegypti* EPV, *Chironomus luridus* EPV, and the like.

Bacterial pathogens suitable for use include, but are not limited to, *Bacillus thuringiensis, Bacillus lentimorbus, Bacillus cereus, Bacillus popilliae, Photorhabdus luminescens, Xenorhabdus nematophilus*, and the like. Fungal pathogens suitable for use include, but are not limited to, *Beauveria bassiana*, Entomophthora spp., *Metarrhizium anisopliae*, and the like.

AcMNPC E2 is described in EP 621337, and co-pending U.S. Ser. No. 08/009,264, filed Jan. 25, 1993, which is incorporated herein by reference. AcMNPV V8 and V8vEGTDEL are described in U.S. Pat. No. 5,662,897 which is incorporated herein by reference. V8vEGTDEL-AaIT is described in EP 697170-A1 and co-pending U.S. Ser. No. 08/322,679, filed Jul. 27, 1994, now U.S. Pat. No. 5,965,123. AcMNPV Px1 is described in co-pending provisional U.S. Ser. No. 60/084,705, filed May 8, 1998, WO 99/58705 which is incorporated herein by reference.

Herbicides suitable for use in the present invention include chemical and biological herbicides. Chemical herbicides include, but are not limited to, dinitro-anilines such as pendimethalin and trifluralin; imidazolinones such as imazethapyr, imazaquin, imazamethabenz-methyl, imazapyr, imazamox and imazapic; haloacetanilides such as alachlor, metolachlor, and propachlor; and the like; and mixtures thereof. Biological herbicides include, but are not limited to, fungal pathogens such as a *Dactylaria higginsii*, and the like, and mixtures thereof.

pH-Dependent polymers suitable for use in the present invention include polymers which are essentially insoluble below about pH 5.5, such as ethyl acrylate/methacrylic acid copolymers, methyl methacrylate/methacrylic acid copolymers, methacrylic acid/methyl acrylate/methyl methacrylate copolymers and the like, and mixtures thereof. Preferred pH-dependent polymers include ethyl acrylate/methacrylic acid copolymers wherein the ratio of free carboxyl groups to esters is about 1:1 (Eudragit® L 30 D, solubilization pH>5.5, available from Röhm Pharma GmbH, Weiterstadt, Germany; and Kollicoat® MAE 30 D, solubilization pH>5.5, available from BASF, Ludwigshafen, Germany), methyl methacrylate/methacrylic acid copolymers wherein the ratio of free carboxyl groups to esters is from about 1:1 to about 1:2 (Eudragit® S100, 1:2 ratio, solubilization pH>7.0, available from Röhm Pharma; and Eudragit® L100, 1:1 ratio, solubilization pH>6.0, available from Röhm Pharma), methacrylic acid/methyl acrylate/methyl methacrylate copolymers wherein the ratio of methacrylic acid, methyl acrylate and methyl methacrylate monomers is about 1:5:2 to 3:7:3 (Preparation 4110D, 1:6.5:2.5 ratio, solubilization pH>7.2, available from Röhm Pharma), and mixtures thereof.

The pH-dependent polymer should be essentially insoluble below about pH 5.5 to prevent premature release of the pesticide when the coated pesticidal matrix is applied to the locus of a pest. In addition, when the pesticidal agent is an insecticide, the pH-dependent polymer should be soluble in the environment of the insect's gut so that the pesticidal agent may be readily released from the coated pesticidal matrix. Preferably, the pH-dependent polymer should be soluble above about pH 7 to ensure that the pesticide is readily released in the insect's gut.

In a preferred embodiment of the process of this invention, the methyl methacrylate/methacrylic acid copolymer is partially solubilized with base to reduce agglomeration of the copolymer particles prior to drying. However, it should be understood that the amount of base added is well below the amount required to fully solubilize the copolymer. Typically, less than about 10% of the free carboxylic acid groups of the copolymer are converted to salts. Bases suitable for use to partially solubilize the methyl methacrylate/methacrylic acid copolymers of this invention include ammonium hydroxide, alkali metal hydroxides, alkaline earth metal hydroxides and the like, with ammonium hydroxide being preferred.

Plasticizers are used in the process of this invention to reduce the minimum film forming temperature of the pH-dependent polymer. Plasticizers suitable for use in the present invention include any of the conventional agents known in the art such as poly(ethylene glycols), poly (propylene glycols), diethyl phthalate, dibutyl phthalate, citric acid esters such as triethyl citrate and the like, castor oil, triacetin and the like or mixtures thereof. Preferred plasticizers include poly(ethylene glycols) having an average molecular weight of about 1,000 to 10,000 and triethyl citrate.

Ultraviolet protectors are used in the present invention to reduce the photoinactivation of the pesticidal agent. Ultraviolet protectors suitable for use include ultraviolet absorbers and ultraviolet reflectors or mixtures thereof. Ultraviolet absorbers include various forms of carbon, such as carbon black (charcoal); benzophenones, such as 2-hydroxy-4-methoxybenzophenone (CYASORB® UV9, available from Cytec Industries, West Paterson, N.J.), 2,2'-dihydroxy-4-methoxybenzophenone (CYASORB® UV24, available from Cytec Industries), 2-hydroxy-4-acryloyloxyethoxybenzophenone (CYASORB® UV2098, available from Cytec Industries), 2-hydroxy-4-n-octoxybenzophenone (CYASORB® UV531, available from Cytec Industries); dyes, such as congo red, malachite green, malachite green hydrochloride, methyl orange, methyl green, brilliant green, acridine yellow, FDC green, FDC yellow, FDC red, and the like. Ultraviolet reflectors include titanium dioxide and the like. Preferred ultraviolet protectors include carbon black, benzophenones, dyes and titanium dioxide; with titanium dioxide, carbon black, CYASORB® UV9 and CYASORB® UV24 being most preferred.

Activity enhancers are used in this invention to enhance pesticidal activity of the pesticidal agent. Activity enhancers suitable for use in this invention include fluorescent brighteners described in U.S. Pat. No. 5,124,149 and stilbene compounds described in U.S. Pat. No. 5,246,936, both incorporated herein by reference. In addition to enhancing pesticidal activity, the stilbene compounds also provide some protection from ultraviolet radiation. Preferred stilbene compounds are the analogues of 4,4'-diamino-2,2'-stilbene disulfonic acid, namely, a Calcofluor White (available from Sigma Chemical Co., St. Louis, Mo.) such as Calcofluor White M2R, Calcofluor White ABT, Calcofluor White LD, Calcofluor White RWP, etc.; a Blancophor (available from Mobay Chemicals, Pittsburgh, Pa.) such as Blancophor BBH, Blancophor MBBH, Blancophor BHC, etc.; an INTRAWITE® (a heterocyclic stilbene derivative, available from Crompton and Knowles Corp., Charlotte, N.C.) such as INTRAWITE® CF, etc.; a Leucophor (available from Sandoz Chemicals Corp., Charlotte, N.C.) such as Leucophor BS, Leucophor BSB, Leucophor EKB, Leucophor PAB, etc.; a Phorwite (available from Mobay Chemicals) such as Phorwite AR, Phorwite BBU, Phorwite BKL, Phorwite CL, Phorwite RKK, etc. and the like. Blancophor BBH, Calcofluor White M2R and Phorwite AR are the most preferred stilbene compounds.

Glidants are used in the process of this invention to keep the dried, coated pesticidal matrix particles from sticking together. In addition, the glidant may also provide some protection from ultraviolet radiation. Glidants suitable for use in this invention include talc, magnesium stearate, calcium stearate, calcium sulfate and the like or mixtures thereof, with talc being preferred.

Other compatible additives such as preservatives, stabilizers (trehalose), anti-foam agents, anti-mold agents, anti-fungal agents, anti-bacterial agents and the like may also be included in the matrices of the present invention. Clearly, anti-fungal agents and anti-bacterial agents generally would not be used when fungal pathogens and bacterial pathogens, respectively, are used.

The present invention also provides wettable powder pesticidal compositions which comprise about 0.5 to 40% by weight of a dispersing agent; about 1 to 10% by weight of a flow enhancing agent; about 10 to 70% by weight of a bulking agent; 0 to about 25% by weight of a wetting agent; 0 to about 35% by weight of a pH-modifying agent; and about 5 to 75% by weight of a coated pesticidal matrix prepared by the process of this invention.

Preferred wettable powder pesticidal compositions of the present invention are those comprising about 2 to 15% by weight of a dispersing agent; about 1 to 10% by weight of a flow enhancing agent; about 10 to 60% by weight of a bulking agent; 0 to about 15% by weight of a wetting agent; 0 to about 20% by weight of a pH-modifying agent; and about 5 to 75% by weight of a coated pesticidal matrix prepared by the process of this invention.

When the pesticidal agent is a biological agent, the wettable powder compositions of this invention preferably comprise about 2 to 10% by weight of a dispersing agent; about 1 to 10% by weight of a flow enhancing agent; about 20 to 50% by weight of a bulking agent; about 2 to 20% by weight of a pH-modifying agent; and about 15 to 60% by weight of a coated biological agent matrix prepared by the process of this invention.

Dispersing agents useful in the wettable powder pesticidal compositions of this invention include any of the conventional agents known in the art. Preferred dispersing agents are anionic agents, such as salts of the condensation products of formaldehyde with the sulfonation products of polycyclic aromatic compounds, sodium lignosulfonate and the like or mixtures thereof with the sodium sulfonate of naphthalene formaldehyde condensates such as MORWET® D425 (available from Witco), LOMAR® PW (available from Henkel, Ambler, Pa.) and DARVAN® 1 (available from R. T. Vanderbilt Co., Norwalk, Conn.) being most preferred.

Flow enhancing agents useful in the wettable powder pesticidal compositions of this invention include conventional flow enhancing agents known in the art with silicates such as calcium silicates being preferred. MICRO-CEL® E (a synthetic calcium silicate hydrate available from Celite Corp., Lompoc, Calif.) is the most preferred flow enhancing agent.

Bulking agents suitable for use in the compositions of the present invention include natural and synthetic clays and silicates, e.g., natural silicas such as diatomaceous earths; magnesium silicates such as talcs; magnesium aluminum silicates such as attapulgites and vermiculites; aluminum silicates such as kaolinites, montmorillonites and micas; and hydrated aluminum silicates such as kaolin clay. Preferred bulking agents are hydrated aluminum silicates, aluminum silicates, magnesium silicates and magnesium aluminum silicates, with kaolin clay being the most preferred bulking agent.

Wetting agents suitable for use in the present invention include any of the conventional agents known in the art. Preferred wetting agents include anionic agents such as sodium N-methyl-N-oleoyltaurate, octylphenoxy polyethoxy ethanol, nonylphenoxy polyethoxy ethanol, sodium dioctyl sulfosuccinate, sodium dodecyl benzene sulfonate, sodium lauryl sulfate, sodium alkyl naphthalene sulfonate, sodium sulfonated alkyl carboxylate and the like or mixtures thereof. A mixture of sodium alkyl naphthalene sulfonate and sodium sulfonated alkyl carboxylate (MORWET® EFW available from Witco, Houston, Tex.) is a highly preferred wetting agent.

pH-Modifying agents are used to maintain the pH of aqueous tank-mixes prepared from the compositions of this invention below about pH 5. pH-Modifying agents suitable for use include, but are not limited to, potassium hydrogen phthalate, and solid organic acids such as citric acid, glutamic acid, maleic acid, d,l-malic acid, glutaric acid, isophthalic acid, succinic acid, fumaric acid, adipic acid, and the like, and mixtures thereof. Citric acid is especially useful as the pH-modifying agent in the compositions of this invention. In the compositions of this invention, it is preferable to use a granular organic acid having a mean particle size greater than about 50 μm, preferably greater than about 100 μm. The use of a granular organic acid improves the storage stability of the wettable powder compositions of this invention when compared to wettable powder compositions containing a micronized organic acid.

The wettable powder pesticidal compositions of the present invention are typically prepared by blending a mixture of a dispersing agent, a bulking agent, a flow enhancing agent, optionally a wetting agent and optionally a pH-modifying agent to form a premix. This premix is then blended with the coated pesticidal matrix to form the desired wettable powder pesticidal compositions of the present invention.

For the control of pests, the wettable powder pesticidal compositions of this invention are diluted with water to form an aqueous tank-mix and the tank-mix is applied to the locus of the pest.

Surprisingly, it has been discovered that the coated pesticidal matrices of this invention provide improved residual control of pests when compared to coated pesticidal agents prepared according to the aqueous coating process described in EP 697170-A1. Accordingly, the present invention provides a method for improving the residual control of a pest by applying to the locus of the pest a pesticidally effective amount of a coated pesticidal matrix prepared by the process of this invention.

Other ingredients such as attractants, stickers, antifoaming agents and the like may also be added to the wettable powder compositions of this invention. However, those additional ingredients are generally added separately to the tank-mix. An adjuvant or mixture of adjuvants may also be added to the tank-mix.

In order to facilitate a further understanding of the invention, the following examples are presented primarily for the purpose of illustrating more specific details thereof. The invention should not be deemed limited thereby except as defined in the claims.

EXAMPLE 1

Preparation of Coated Pesticidal Matrices Using an Ethyl Acrylate/methacrylic Acid Copolymer A mixture of V8vEGTDEL polyhedral inclusion bodies (PIBs) (12.43 g of technical material, 7.5 g of PIBs, about $1.27\times10^{11}$ PIBs/gram, mean PIB size about 2.5 μm), water (65.02 g), Blancophor BBH (28.04 g, mean particle size about 1 μm), PEG 5000 (poly(ethylene glycol) average MW 5000, 14.0 g of a 10 wt/wt % solution), and Kollicoat® MAE 30 D (46.71 g) is stirred to obtain a slurry. The slurry is filtered through an 80 mesh screen and spray dried using a Büchi spray drier (model 190) to obtain the coated pesticidal matrix identified as composition 1 in Table II.

Using essentially the same procedure, but using the ingredients listed in Table I, the coated pesticidal matrices identified as compositions 2–17 in Table II are prepared.

TABLE I

| | |
|---|---|
| **Pesticidal Agent** | |
| a. | V8vEGTDEL polyhedral inclusion bodies |
| b. | V8vEGTDEL-AaIT polyhedral inclusion bodies |
| c. | Hydramethylnon |
| d. | *Bacillus thuringiensis* |
| **Ethyl Acrylate/Methacrylic Acid Copolymer** | |
| e. | Kollicoat ® MAE 30 D |
| f. | Eudragit ® L 30 D |
| **Plasticizer** | |
| g. | PEG 5000 |
| h. | PEG 8000 |
| **Stilbene Compound** | |
| i. | Blancophor BBH |
| j. | Calcofluor M2R |
| **UV-Protector** | |
| k. | Titanium dioxide |
| l. | Charcoal |
| **Additional Compound** | |
| m. | Antifoam A ® (a polydimethylsiloxane and silica antifoam agent available from Dow Corning, Midland, Michigan) |

TABLE II

Pesticidal Matrices

| | Ingredient/wt/wt % | | | | | |
|---|---|---|---|---|---|---|
| Composition | Pesticidal Agent | Copolymer | Plasticizer | Stilbene Compound | UV-Protector | Additional Compound |
| 1 | a/11.25 | e/28.62 | g/2.86 | i/57.27 | — | — |
| 2 | a/12.23 | f/23.30 | g/2.33 | i/62.14 | — | — |
| 3 | a/12.25 | f/18.37 | — | i/69.39 | — | — |
| 4 | a/16.19 | f/20.96 | h/1.19 | i/61.65 | — | — |
| 5 | a/20.38 | f/26.38 | h/1.50 | — | k/51.73 | — |
| 6 | a/33.31 | f/43.11 | h/2.45 | j/21.13 | — | — |
| 7 | a/16.00 | f/20.71 | h/2.36 | i/60.93 | — | — |
| 8 | a/13.30 | f/17.22 | h/1.96 | i/25.32 | k/42.20 | — |
| 9 | a/20.55 | f/25.74 | h/1.49 | — | k/52.22 | — |

TABLE II-continued

| Pesticidal Matrices | | | | | | |
|---|---|---|---|---|---|---|
| | Ingredient/wt/wt %[1] | | | | | |
| Composition | Pesticidal Agent | Copolymer | Plasticizer | Stilbene Compound | UV-Protector | Additional Compound |
| 10 | a/16.11 | f/20.44 | g/2.05 | i/61.40 | — | — |
| 11 | a/12.22 | f/23.29 | g/2.33 | i/62.16 | — | — |
| 12 | a/13.90 | f/26.52 | g/2.62 | i/49.93 | l/7.02 | — |
| 13 | a/21.28 | f/19.17 | g/1.92 | i/57.64 | — | — |
| 14 | b/14.16 | f/27.05 | g/2.13 | i/56.66 | — | — |
| 15 | b/15.06 | e/22.77 | g/2.23 | i/59.94 | — | — |
| 16 | c/13.95 | f/27.91 | g/2.33 | i/55.81 | — | — |
| 17 | d/14.15 | f/27.02 | g/2.06 | i/56.61 | — | m/0.16 |

[1]Compositions may contain a small amount of residual water.

EXAMPLE 2

Preparation of Coated Pesticidal Matrices Using a Methyl Methacrylate/methacrylic Acid Copolymer A slurry is prepared by sequentially mixing V8vEGTDEL polyhedral inclusion bodies (13.0 g of technical material, 6.0 g of PIBs, about $1.27\times10^{11}$ PIBs/gram, mean PIB size about 2.5 $\mu$m), water, 56.6 g of a copolymer slurry (previously prepared by mixing Eudragit® S100 (30.0 g), water (166 g), 1 N ammonium hydroxide solution (15.24 g) and triethyl citrate (15.0 g)), Blancophor BBH (14.0 g), talc (3.21 g), charcoal (9.0 g), a solution of Calcofluor M2R (14.0 g) in water, and water. The resultant slurry is then filtered through an 80 mesh screen and spray dried using a Büchi spray drier (model 190) to obtain the coated pesticidal matrix identified as composition 18 in Table IV.

Using essentially the same procedure, but using the ingredients listed in Table III, the coated pesticidal matrices identified as compositions 19–26 in Table IV are prepared.

TABLE III

| | |
|---|---|
| Pesticidal Agent | |
| a. | V8vEGTDEL polyhedral inclusion bodies |
| b. | V8vEGTDEL-AaIT polyhedral inclusion bodies |
| c. | Yeast |
| Methyl Methacrylate/Methacrylic Acid Copolymer | |
| d. | Eudragit ® S100 |
| e. | Eudragit ® L100 |
| Plasticizer | |
| f. | Triethyl citrate |
| UV-Protector | |
| g. | Charcoal |
| Stilbene Compound | |
| h. | Blancophor BBH |
| i. | Calcofluor M2R |
| Glidant | |
| j. | Talc |
| Additional Compound | |
| k. | Citric acid |
| l. | Microat ® afa Complex (an antioxidant available from Nurture Inc., Missoula, Montana) |

TABLE IV

| Pesticidal Matrices | | | | | | | |
|---|---|---|---|---|---|---|---|
| | Ingredient/wt/wt %[1] | | | | | | |
| Composition | Pesticidal Agent | Copolymer | Plasticizer | UV-Protector | Stilbene Compound | Glidant | Additional Compound |
| 18 | a/11.89 | d/14.86 | f/7.43 | g/17.84 | h/27.75 i/13.87 | j/6.36 | — |
| 19 | a/11.89 | d/14.86 | f/7.43 | g/17.84 | h/35.08 i/6.54 | j/6.36 | — |
| 20 | a/12.36 | e/15.45 | f/7.72 | g/18.54 | h/37.08 | j/7.72 | k/1.13 |
| 21 | a/12.12 | e/15.15 | f/7.58 | g/18.18 | h/36.36 | j/7.58 | k/1.01 l/2.02 |
| 22 | b/10.90 | d/16.59 | f/8.30 | g/16.59 | h/38.06 i/4.36 | j/5.20 | — |
| 23 | b/8.68 | d/17.59 | f/8.81 | g/16.77 | h/38.47 i/4.41 | j/5.26 | — |
| 24 | b/8.77 | d/16.94 | f/8.47 | g/17.20 | h/38.86 i/4.45 | j/5.31 | — |
| 25 | a/10.90 | d/16.59 | f/8.30 | g/16.59 | h/38.06 i/4.36 | j/5.20 | — |
| 26 | c/21.61 | e/40.36 | — | — | h/38.04 | — | — |

[1]Compositions may contain a small amount of residual water.

EXAMPLE 3

Preparation of Coated Pesticidal Matrices Using a Methacrylic Acid/methyl Acrylate/methyl Methacrylate Copolymer A mixture of chlorfenapyr (3.00 g, mean particle size about 2.5 μm), water (100.00 g), Blancophor BBH (12.00 g, mean particle size about 1 μm), triethyl citrate (0.23 g), a 20% solution of Preparation 4110D (22.50 g), talc (3.00 g), and MORWET® D425 (1.50 g) is stirred to obtain a slurry. The slurry is filtered through an 80 mesh screen and spray dried using a Büchi spray drier (model 190) to obtain the coated pesticidal matrix identified as composition 27 in Table VI.

Using essentially the same procedure, but using the ingredients listed in Table V, the coated pesticidal matrices identified as compositions 28–32 in Table VI are prepared.

TABLE V

| | |
|---|---|
| **Pesticidal Agent** | |
| a. | Chlorfenapyr |
| b. | Hydramethylnon |
| c. | 1-(6-Chloro-3-pyridyl)-2-(nitromethylene) imidazolidine |
| d. | V8vEGTDEL-AaIT polyhedral inclusion bodies |
| **Methacrylic Acid/Methyl Acrylate/Methyl Methacrylate Copolymer** | |
| Preparation 4110D | |
| **Plasticizer** | |
| Triethyl citrate | |
| **Stilbene Compound** | |
| e. | Blancophor BBH |
| f. | Calcofluor M2R |
| **UV-Protector** | |
| Charcoal | |
| **Glidant** | |
| Talc | |
| **Additional Compound** | |
| MORWET ® D425 | |

EXAMPLE 4

Preparation of a Coated Pesticidal Matrix Using a Methyl Methacrylate/methacrylic Acid Copolymer, REAX® 85A and Indulin® C A mixture of V8vEGTDEL polyhedral inclusion bodies (13.0 g of technical material, 6.0 g of PIBs, about $1.27\times10^{11}$ PIBs/gram, mean PIB size about 2.5 μm) and ammonium hydroxide solution (15.0 g, pH 9.5) is stirred for 15 minutes, treated with REAX® 85A (0.18 g, a sodium lignosulfonate available from Westvaco, Charleston Heights, S.C.), stirred for 15 minutes, treated with Indulin® C (12.0 g of a 2% solution, pH 11, a sodium lignate available from Westvaco), stirred for one hour, and adjusted slowly to pH 4.5 with dilute sulfuric acid over 2.5 hours. After stirring for 45 minutes, the polyhedral inclusion body mixture is mixed with the copolymer slurry described in Example 2 (56.6 g), Blancophor BBH (14.70 g), talc (3.21 g), charcoal (9.0 g), a solution of Calcofluor M2R (3.30 g) in water, and water to obtain a slurry. The slurry is filtered through an 80 mesh screen and spray dried using a Büchi spray drier (model 190) to obtain the coated pesticidal matrix identified as composition 33 in Table VII.

TABLE VII

| Composition 33 | |
|---|---|
| Ingredient | wt/wt % |
| V8vEGTDEL polyhedral inclusion bodies | 12.53 |
| Eudragit ® S100 | 15.66 |
| Triethyl citrate | 7.83 |
| Charcoal | 18.80 |
| Blancophor BBH | 30.70 |
| Calcofluor M2R | 6.89 |
| Talc | 6.70 |
| Indulin ® C | 0.50 |
| REAX ® 85A | 0.38 |

EXAMPLE 5

Preparation of Wettable Powder Pesticidal Compositions

The coated pesticidal matrix identified as composition 18 in Table IV (23.13 g) is added to a premix of MORWET® EFW (3.84 g), MORWET® D425 (7.68 g), kaolin clay

TABLE VI

| | Pesticidal Matrices | | | | | | |
|---|---|---|---|---|---|---|---|
| | Ingredient/wt/wt %[1] | | | | | | |
| Composition | Pesticidal Agent | Preparation 4110D | Triethyl Citrate | Stilbene Compound | Charcoal | Talc | MORWET ® D425 |
| 27 | a/12.38 | 18.57 | 0.95 | e/49.53 | — | 12.38 | 6.19 |
| 28 | a/9.01 | 18.02 | 0.90 | e/36.04<br>f/9.01 | 13.51 | 9.01 | 4.50 |
| 29 | b/12.38 | 18.57 | 0.95 | e/49.53 | — | 12.38 | 6.19 |
| 30 | b/9.01 | 18.02 | 0.90 | e/36.04<br>f/9.01 | 13.51 | 9.01 | 4.50 |
| 31 | c/13.97 | 21.12 | 1.05 | e/42.76 | — | 13.97 | 7.13 |
| 32 | d/9.36 | 18.71 | 1.87 | e/37.42<br>f/4.57 | 18.71 | 9.36 | — |

[1]Compositions may contain a small amount of residual water.

(23.03 g), MICRO-CEL® E (2.30 g), and citric acid (11.52 g). The resultant mixture is blended to obtain the wettable powder composition identified as composition 34 in Table VIII.

Using essentially the same procedure, the wettable powder compositions identified as compositions 35–53 in Table VIII are prepared.

TABLE VIII

Wettable Powder Pesticidal Compositions

| Composition | Coated Pesticidal Matrix[1] | MORWET ® EFW | MORWET ® D425 | Kaolin Clay | MICRO-CEL ® E | Citric Acid |
|---|---|---|---|---|---|---|
| | Ingredient/wt/wt % | | | | | |
| 34 | 18/32.35 | 5.37 | 10.74 | 32.21 | 3.22 | 16.11[2] |
| 35 | 1/30.77 | 5.50 | 10.99 | 32.97 | 3.30 | 16.48[2] |
| 36 | 2/25.91 | 5.88 | 11.76 | 35.29 | 3.53 | 17.63[2] |
| 37 | 9/16.05 | 6.67 | 13.32 | 39.98 | 4.00 | 19.99[2] |
| 38 | 11/25.91 | 5.88 | 11.76 | 35.28 | 3.53 | 17.64[2] |
| 39 | 12/16.98 | 7.56 | 15.11 | 49.81 | 4.98 | 5.56[2] |
| 40 | 13/19.80 | 6.37 | 12.73 | 38.20 | 3.82 | 19.09[2] |
| 41 | 15/21.52 | 7.13 | 14.30 | 47.10 | 4.70 | 5.25[2] |
| 42 | 19/32.35 | 5.37 | 10.74 | 32.21 | 3.22 | 16.11[2] |
| 43 | 20/31.12 | 5.47 | 10.94 | 32.79 | 3.28 | 16.40[2] |
| 44 | 21/31.73 | 5.42 | 10.84 | 32.50 | 3.25 | 16.25[2] |
| 45 | 22/30.70 | 5.50 | 11.00 | 32.99 | 3.30 | 16.50[2] |
| 46 | 22/33.47 | 5.70 | 11.40 | 36.16 | 3.61 | 9.66[2] |
| 47 | 22/32.79 | 5.34 | 10.67 | 32.01 | 3.20 | 16.00[2] |
| 48 | 23/31.94 | 5.52 | 11.04 | 36.39 | 3.64 | 11.47[2] |
| 49 | 25/33.86 | 6.02 | 12.04 | 39.68 | 3.97 | 4.43[2] |
| 50 | 27/43.86 | 5.11 | 10.22 | 33.68 | 3.37 | 3.76[2] |
| 51 | 28/60.42 | 3.60 | 7.20 | 23.75 | 2.37 | 2.65[2] |
| 52 | 31/38.76 | 5.00 | 10.00 | 32.94 | 3.30 | 10.00[3] |
| 53 | 32/42.80 | — | 3.00 | 37.20 | 6.00 | 11.00[3] |

[1]The coated pesticidal matrix is identified by the composition number from Tables II, IV or VI.
[2]Mean particle size about 1–3 μm.
[3]Mean particle size greater than about 100 μm.

EXAMPLE 6

Evaluation of Wettable Powder Pesticidal Compositions of this Invention and a Wettable Powder Pesticidal Composition Disclosed in EP 697170-A1 Against Tobacco Budworms Wettable powder compositions 34, 36, 37 and 43, and a control composition, identified below, are tested for efficacy against neonate tobacco budworms, *H. virescens*, on cotton variety IAC-22 through bioassay of field-treated foliage. Each composition is mixed with water, 0.2 w/v % KINETIC® (nonionic surfactant mixture available from Helena Chemical Co., Memphis, Tenn.), and 3.5 w/v % MIRASPERSE® (2-hydroxypropyl ether starch available from A.E. Staley Manufacturing Co., Decatur, Ill.). In addition, 0.1 w/v % citric acid is added to the aqueous control composition. Treatments are applied with a $CO_2$ backpack sprayer calibrated to deliver 200 L/ha using 2 ft boom with hollow-cone nozzles (3/row; 1 centered and 2 drop).

For bioassay, leaves are collected 1–2 hours following application for initial activity and 1, 2, 3, and 4 days after treatment for residual activity. The treated leaves are placed in petri dishes with moist filter papers (1 leaf/dish; 4 larvae/dish; 16 dishes/—treatment with a total of 64 larvae/treatment/sampling period). After allowing the larvae to feed on the treated leaves for four days, they are transferred to diet trays containing pieces of untreated cotton leaves; one larva/cell. After 4 days, the surviving larvae are counted. The results are summarized in Table IX.

As can be seen from the data in Table IX, compositions containing coated pesticidal matrices prepared by the process of the present invention, in general, have greater residual activity against *H. virescens* than the control composition prepared by the aqueous process described in EP 697170-A1. In particular, composition 34 has significantly greater residual activity than the control composition. This is an especially surprising discovery because the copolymer used in composition 34 and the control composition is the same Eudragit® S100.

Control Composition

| Ingredient | wt/wt % |
|---|---|
| [1]Coated pesticidal agent | 25.14 |
| MORWET ® EFW | 5.94 |
| MORWET ® D425 | 11.89 |
| Kaolin Clay | 35.64 |
| MICRO-CEL ® E | 3.56 |
| Citric Acid | 17.83 |

[1]Prepared according to the aqueous process described in EP 697170-A1. The coated pesticidal agent contains 15.31 wt/wt % V8vEGTDEL polyhedral inclusion bodies, 15.31 wt/wt % Eudragit ® S100, 0.43 wt/wt % PEG 8000, 23.04 wt/wt % charcoal and 45.92 wt/wt % Blancophor BBH.

TABLE IX

Percent Mortality of *H. virescens* on Cotton variety IAC-22

| Treatment | Days After Treatment 0 | 1 | 2 | 3 | 4 |
|---|---|---|---|---|---|
| Composition 34 | 100 | 92 | 95 | 89 | 75 |
| Composition 36 | 98 | 97 | 77 | 75 | 66 |
| Composition 37 | 97 | 94 | 92 | 77 | 67 |
| Composition 43 | 98 | 95 | 95 | 86 | 80 |
| Control composition | 95 | 86 | 83 | 73 | 69 |
| Untreated | 5 | 2 | 5 | 8 | 6 |

EXAMPLE 7

Evaluation of Wettable Powder Pesticidal Compositions Against Tobacco Budworms on Cotton and Lettuce Compositions 39 and 49 from Table VIII are tested for efficacy against neonate tobacco budworms, *Heliothis virescens*, on lettuce variety Green-Towers and cotton variety Delta-Pine 51 through bioassay of field-treated foliage. The plots are strips of cotton and lettuce (ca. 40 ft long) with 3 ft row spacing. Each composition is mixed with water and applied at $8\times10^{11}$ polyhedral inclusion bodies/acre. DIPEL® 2X (*Bacillus thuringiensis* var. Kurstaki, available from Abbott Laboratories, North Chicago, Ill.) is applied at 1.0 lb product/acre as a standard. Treatments are applied with a $CO_2$ backpack sprayer calibrated to deliver 20 gallons per acre using a 2 ft boom with hollow-cone nozzles (3/row; 1 centered and 2 drop).

For bioassay, leaves are collected 1–2 hours following application for initial activity and 2, 3, 4 and 5 days after treatment for residual activity. The treated leaves are placed in petri dishes with moist filter papers (1 leaf/dish; 4 larvae/dish; 16 dishes/—treatment with a total of 64 larvae/treatment/sampling period). After allowing the larvae to feed on the treated leaves for two days, they are transferred to diet trays; one larva/cell. The surviving larvae are also counted at 2, 4, 6 and 8 days after transfer to diet. The results are summarized in Tables X and XI. As can be seen from the data in Tables X and XI, the pesticidal compositions of this invention (compositions 39 and 49) have greater residual activity against tobacco budworms after 4, 6 and 8 days on diet than DIPEL® 2X.

TABLE X

Percent Mortality of Tobacco Budworms on Cotton

| Treatment | Days After Transfer to Diet | Days After Treatment 0 | 2 | 3 | 4 | 5 |
|---|---|---|---|---|---|---|
| Composition 39 | 0 | 4 | 3 | 2 | 1 | 2 |
| | 2 | 24 | 9 | 6 | 3 | 4 |
| | 4 | 49 | 23 | 14 | 6 | 13 |
| | 6 | 50 | 27 | 16 | 7 | 15 |
| | 8 | 51 | 27 | 16 | 8 | 15 |
| Composition 49 | 0 | 2 | 3 | 2 | 0 | 5 |
| | 2 | 52 | 17 | 9 | 7 | 6 |
| | 4 | 90 | 57 | 29 | 11 | 14 |
| | 6 | 91 | 59 | 31 | 15 | 16 |
| | 8 | 91 | 59 | 33 | 16 | 16 |
| DIPEL ® 2X | 0 | 29 | 9 | 6 | 2 | 4 |
| | 2 | 37 | 13 | 7 | 4 | 6 |
| | 4 | 56 | 14 | 10 | 4 | 6 |
| | 6 | 56 | 14 | 12 | 5 | 6 |
| | 8 | 56 | 14 | 12 | 5 | 6 |
| Untreated | 0 | 1 | 2 | 1 | 1 | 2 |
| | 2 | 1 | 4 | 2 | 3 | 4 |
| | 4 | 2 | 6 | 3 | 3 | 5 |
| | 6 | 2 | 6 | 4 | 3 | 5 |
| | 8 | 2 | 6 | 4 | 3 | 5 |

TABLE XI

Percent Mortality of Tobacco Budworms on Lettuce

| Treatment | Days After Transfer to Diet | Days After Treatment 0 | 2 | 3 | 4 | 5 |
|---|---|---|---|---|---|---|
| Composition 39 | 0 | 27 | 5 | 2 | 5 | 1 |
| | 2 | 72 | 36 | 16 | 20 | 11 |
| | 4 | 94 | 84 | 62 | 55 | 50 |
| | 6 | 95 | 85 | 67 | 59 | 52 |
| | 8 | 95 | 86 | 67 | 60 | 52 |
| Composition 49 | 0 | 16 | 3 | 7 | 1 | 6 |
| | 2 | 73 | 24 | 23 | 18 | 16 |
| | 4 | 98 | 88 | 78 | 62 | 55 |
| | 6 | 99 | 88 | 85 | 62 | 58 |
| | 8 | 99 | 88 | 85 | 62 | 59 |
| DIPEL ® 2X | 0 | 100 | 53 | 42 | 45 | 29 |
| | 2 | 100 | 70 | 50 | 57 | 35 |
| | 4 | 100 | 70 | 56 | 58 | 37 |
| | 6 | 100 | 70 | 56 | 58 | 38 |
| | 8 | 100 | 70 | 56 | 58 | 38 |
| Untreated | 0 | 2 | 1 | 2 | 2 | 4 |
| | 2 | 2 | 2 | 5 | 2 | 6 |
| | 4 | 4 | 5 | 6 | 3 | 9 |
| | 6 | 4 | 5 | 6 | 4 | 10 |
| | 8 | 4 | 5 | 6 | 6 | 10 |

EXAMPLE 8

Evaluation of Non-irradiated and Irradiated Wettable Powder Compositions Against *Heliothis virescens*

Plastic bioassay trays containing 32 open-faced wells (4×4×2.5 cm, L×W×H) per tray are utilized as test arenas in this evaluation. Five mL of Stoneville diet (soybean/wheat germ) is poured into each well and allowed to harden. Aqueous suspensions of the wettable powder pesticidal compositions are evenly spread over the surface of the hardened diet to provide $2\times10^3$ V8vEGTDEL polyhedral inclusion bodies per well. Half of the trays are placed under ultraviolet lamps (two FS40UVB bulbs set 30 cm above the trays, Atlantic Ultraviolet Corp., Bay Shore, N.Y.) for four hours. All trays are then infested with one three-day-old *H. virescens* larva per well. The wells are covered with a vented, clear plastic sheet and held under constant fluorescent light at a temperature of about 27° C. After ten days, the wells are examined and larval mortality measurements are made. The results are summarized in Table XII.

Advantageously, the wettable powder pesticidal compositions of this invention (composition numbers 35, 36, 38 and 40) retain at least 73 percent of their original activity after being exposed to ultraviolet light for 4 hours.

TABLE XII

Evaluation Of Non-Irradiated and Irradiated Wettable Powder Pesticidal Compositions Against *H. Virescens*

| Wettable Powder Composition[1] | Irradiation Exposure (hours) | Percent Larval Mortality |
|---|---|---|
| 35 | 0 | 98 |
| | 4 | 74 |
| 36 | 0 | 98 |
| | 4 | 80 |
| 38 | 0 | 97 |
| | 4 | 75 |
| 40 | 0 | 97 |
| | 4 | 71 |

[1]Composition number from Table VIII.

EXAMPLE 9

Field Evaluation of Wettable Powder Pesticidal Compositions Against Tobacco Budworms on Tobacco in North Carolina A field evaluation is conducted on tobacco grown near Clayton, N.C. A wettable powder composition of this invention (composition 46) at $2\times10^{11}$, $5\times10^{11}$, and $8\times10^{11}$ bodies/acre, *Bacillus thuringiensis* (DIPEL® 2X, Abbott Laboratories) at 1.0 lb wettable powder (WP)/acre, and acephate (ORTHENE® 75SP, available from Valent USA, Walnut Creek, Calif.) at 0.75 lb active ingredient (ai)/acre are compared for efficacy against *H. virescens*. Biological materials are suspended in water containing an insect gustatory stimulant (PHEAST® available from AGRISENSE, Fresno, Calif.); aqueous dilutions of acephate contained no PHEAST®. Treatments and untreated check are replicated four times (small plots) in a randomized complete block design. By using fine-hair brushes, 1- to 2-day old laboratory-reared *H. virescens* are placed on the underside of leaves in each plot. Natural infestation of *H. virescens* also occurred at the test site. Treatments are applied to tobacco about 2 hours before each artificial larval infestation on days 1 and 8. Treatments are applied with a tractor-mounted, $CO_2$-pressurized boom sprayer which is calibrated to deliver 25 gallons/acre through a single D2-33 nozzle centered over each tobacco row. Boom pressure during application is 60 $lb/in^2$.

At 2 and 5 days after first application and 5 and 9 days after second application, live *H. virescens* are counted on 20 plants in each plot. Additionally, visual estimate of leaf damage caused by larval feeding is made 14 days after the second application using the rating scale shown below. The results are summarized in Table XIII.

Rating Scale

| Rating | Meaning |
|---|---|
| 4 | Severe Damage |
| 3 | Heavy Damage |
| 2 | Moderate Damage |
| 1 | Slight Damage |
| 0 | No Damage |

As can be seen from the data in Table XIII, the wettable powder composition of this invention (composition 46) provides good control of *H. virescens* on tobacco. In fact, on day 17 of the test, the invention composition provides greater control of *H. virescens* than DIPEL® 2X and acephate.

TABLE XIII

Field Evaluation of Wettable Powder Compositions - North Carolina

| | | Mean Number of Live Larvae per 20 Plants Day of Test | | | | Mean Plant Injury on Day |
|---|---|---|---|---|---|---|
| Treatment | Rate | 3 | 8 | 13 | 17 | 22 of Test |
| Composition | $2\times10^{11}$ bodies/acre | 7.8 | 6.2 | 1.8 | 0.5 | 0.4 |
| 46 | 5 × 10 bodies/acre | 6.8 | 6.2 | 1.2 | 0.2 | 0.3 |
| | 8 × 10 bodies/acre | 7.0 | 6.0 | 1.0 | 0.5 | 0.3 |
| DIPEL ® 2X | 1.0 lb of WP/acre | 5.5 | 5.0 | 1.2 | 2.5 | 0.1 |
| Acephate | 0.75 lb of ai/acre | 6.0 | 5.8 | 1.2 | 0.8 | 0.2 |
| Untreated | | 11.2 | 8.2 | 8.8 | 9.0 | 1.8 |

EXAMPLE 10

Field Evaluation of Wettable Powder Pesticidal Compositions Against Tobacco Budworms on Tobacco in Georgia A field evaluation is conducted on flue-cured tobacco (var. K-236) grown near Tifton, Ga. A wettable powder composition of this invention (composition 47) at $2\times10^{11}$, $5\times10^{11}$, and $8\times10^{11}$ bodies/acre, *Bacillus thuringiensis* (DIPEL® 4L, available from Abbott Laboratories) at 1.0 pint/acre, and methomyl (LANNATE® 2.4L, available from DuPont, Wilmington, Del.) at 0.6 lb active ingredient (ai)/acre are compared for efficacy against *H. virescens*. Biological materials are suspended in water containing an insect gustatory stimulant (COAX® available from CCT Corp., Carlsbad, Calif.) at 2.0 pints/acre; aqueous dilutions of methomyl contained no COAX®. Treatments and untreated check are replicated four times in a randomized complete block design. A treatment replicate consists of a five-row by 20 ft plot of tobacco. Treatments are applied to tobacco on days 1, 5, 9, 17 and 22 of the test. Treatments are applied with a backpack, $CO_2$-pressurized boom sprayer which is calibrated to deliver 20.7 gallons/acre through three TX12 (Spraying Systems, Wheaton, Ill.) hollow-cone nozzles per row (one nozzle above center of the row and one nozzle directed at each of the two sides of the row). Boom pressure during application is 40 $lb/in^2$.

On days 5, 8, 12, 22, 26 and 29 of the test, live *H. virescens* are counted on 20 plants in each plot. The results are summarized in Table XIV.

As can be seen from the data in Table XIV, the wettable powder composition of this invention (composition 47) provides good control of *H. virescens*.

EXAMPLE 11

Evaluation of UV Stability of Wettable Powder Compositions Comprising Chlorfenapyr Wettable powder compositions 50 and 51 from Table VIII, and a control composition identified below are evaluated for UV stability. An aqueous suspension of each test composition is applied to plastic petri dishes (100 mm×15 mm) using a belt sprayer with nozzles calibrated to provide 400 l/ha. The test materials are applied at rates to provide the equivalent of 0.5, 1.0 and 5.0 g of chlorfenapyr per hectare. The dishes are dried and exposed to UV light using either a UV-B lamp (280–315 nm) or natural light for various periods of time. Three second-instar tobacco budworm larvae (*Heliothis virescens*) are then placed in each dish and the dishes are covered. After holding the dishes at 26.7° C. for 48 hours, the surviving larvae are counted. The results are summarized in Tables XV and XVI.

As can be seen from the data in Tables XV and XVI, chlorfenapyr treatments made with the wettable powder compositions of this invention are significantly more stable to UV exposure than the control composition which does not incorporate chlorfenapyr into a pesticidal matrix.

Control Composition

| Ingredient | wt/wt % |
|---|---|
| Chlorfenapyr (tech.) | 5.43 |
| MORWET ® EFW | 8.60 |
| MORWET ® D425 | 17.21 |
| Kaolin Clay | 56.75 |

-continued

| Control Composition | |
|---|---|
| Ingredient | wt/wt % |
| MIRO-CEL ® E | 5.67 |
| Citric Acid[1] | 6.34 |

[1]Mean particle size about 1–3 μm

TABLE XV

Evaluation of UV (natural light) Irradiated Chlorfenapyr Wettable Powder Compositions

| | Irradiation Exposure (days) | Percent Larval Mortality 1.0 g/ha | Percent Larval Mortality 0.5 g/ha |
|---|---|---|---|
| Wettable Powder Composition | | | |
| 50 | 0 | 100 | 86 |
| | 2 | 74 | 58 |
| | 3 | 28 | 34 |
| 51 | 0 | 100 | 91 |
| | 2 | 100 | 75 |
| | 3 | 63 | 48 |
| Control Composition | 0 | 100 | 97 |
| | 2 | 54 | 34 |
| | 3 | 15 | 22 |

TABLE XVI

Evaluation of UV-B Lamp Irradiated Chlorfenapyr Wettable Powder Compositions

| | Irradiation Exposure (hours) | Percent Larval Mortality 5.0 g/ha | Percent Larval Mortality 1.0 g/ha |
|---|---|---|---|
| Wettable Powder Composition | | | |
| 50 | 0 | 100 | 100 |
| | 8 | 100 | 76 |
| | 22 | 100 | 76 |
| | 37 | 100 | 0 |
| 51 | 0 | 100 | 100 |
| | 8 | 100 | 47 |
| | 22 | 100 | 21 |
| | 37 | 56 | 0 |
| Control Composition | 0 | 100 | 100 |
| | 8 | 100 | 31 |
| | 22 | 100 | 24 |
| | 37 | 14 | 6 |

We claim:

1. A process for preparing a coated pesticidal matrix which includes a pesticidal agent which itself is substantially inactivated by ultra-violet radiation, but which when included in said coated matrix retains a significant amount of its original pesticidal activity, which process consists essentially of (a) preparing an aqueous mixture containing said pesticidal agent, a pH-dependent polymer selected from the group consisting of ethyl acrylate/methacrylic acid copolymers, methyl methacrylate/methacrylic acid copolymers, methacrylic acid/methyl acrylate/methyl methacrylate copolymers and mixtures thereof, a base, optionally a plasticizer, optionally an ultraviolet protector, optionally an activity enhancer, optionally a glidant, and water;

wherein the polymer (1) contains ester groups and free carboxylic acid groups, (2) is partially solubilized due to the action of the base, and (3) has solubilization pH greater than pH 5.5;

wherein the amount of base added is well below the amount required to fully solubilize the copolymer such that no more than 10% of the free carboxylic acid groups of the copolymer are converted to salts;

wherein the mixture's pH is less than the polymer's solubilization pH; and (b) drying the mixture to produce a coated pesticidal matrix.

2. A process as described in claim 1 wherein the polymer is soluble above pH 7.

3. A process as described in claim 1, wherein the base is a hydroxide compound.

4. A process as described in claim 3, wherein the base is selected from the group consisting of ammonium hydroxide, an alkali metal hydroxide, an alkaline earth metal hydroxide, and mixtures thereof.

5. A process as described in claim 4, wherein the base is ammonium hydroxide.

6. A process as described in claim 1, wherein the mixture does not contain the plasticizer, the ultraviolet protector, the activity enhancer, and the glidant.

7. A process as described in claim 1, wherein the mixture contains the plasticizer.

8. A process as described in claim 1, wherein the mixture contains the ultraviolet protector.

9. A process as described in claim 1, wherein the mixture contains the activity enhancer.

10. A process as described in claim 1, wherein the mixture contains the glidant.

11. A process as described in claim 1, wherein the mixture contains the plasticizer and the ultraviolet protector.

12. A process as described in claim 1, wherein the mixture contains the plasticizer and the activity enhancer.

13. A process as described in claim 1, wherein the mixture contains the plasticizer and the glidant.

14. A process as described in claim 1, wherein the mixture contains the ultraviolet protector and the activity enhancer.

15. A process as described in claim 1, wherein the mixture contains the ultraviolet protector and the glidant.

16. A process as described in claim 1, wherein the mixture contains the activity enhancer and the glidant.

17. A process as described in claim 1, wherein the mixture contains the plasticizer, the ultraviolet protector, and the activity enhancer.

18. A process as described in claim 1, wherein the mixture contains the ultraviolet protector, the activity enhancer, and the glidant.

19. A process as described in claim 1, wherein the mixture contains the plasticizer, the activity enhancer, and the glidant.

20. A process as described in claim 1, wherein the mixture contains the plasticizer, the ultraviolet protector, and the glidant.

21. A process as described in claim 1, wherein the mixture contains the plasticizer, the ultraviolet protector, the activity enhancer, and the glidant.

22. A process as described in claim 1, wherein the pesticidal agent is selected from the group consisting of an insecticide, an acaricide, a nematicide, a fungicide, a herbicide, and mixtures thereof.

23. A process as described in claim 22, wherein the pesticidal agent is an insecticide selected from the group consisting of a chemical insecticide, a biological insecticide, and mixtures thereof.

24. A process as described in claim 23, wherein the insecticide is a biological insecticide.

25. A process as described in claim 24, wherein the biological insecticide is a naturally-occurring or a genetically-modified variety of an insect biological control agent.

26. A process as described in claim 25, wherein the insect biological control agent is selected from the group consisting of a viral pathogen, a bacterial pathogen, a fungal pathogen, and mixtures thereof.

27. A process as described in claim 26, wherein the insect biological control agent is a viral pathogen selected from the group consisting of a DNA virus, a RNA virus, an unclassified insect virus, and mixtures thereof.

28. A process as described in claim 27, wherein the viral pathogen is a DNA virus selected from the group consisting of a double stranded enveloped DNA virus, a double stranded nonenveloped DNA virus, a single stranded DNA virus, and mixtures thereof.

29. A process as described in claim 28, wherein the DNA virus is a double stranded enveloped DNA virus selected from the group consisting of Entomopoxvirinae and Eubaculovirinae.

30. A process as described in claim 29, wherein the double stranded enveloped DNA virus is Entomopoxvirinae.

31. A process as described in claim 30, wherein the double stranded enveloped DNA virus Entomopoxvirinae is an entomopox virus (EPV) selected from the group consisting of *Melolontha melolontha* EPV, *Amsacta moorei* EPV, *Locusta migratoria* EPV, *Melanoplus sanguinipes* EPV, *Schistocerca gregaria* EPV, *Aedes aegypti* EPV, *Chironomus luridus* EPV, and mixtures thereof.

32. A process as described in claim 29, wherein the double stranded enveloped DNA virus is Eubaculovirinae.

33. A process as described in claim 32, wherein the double stranded enveloped DNA virus Eubaculovirinae is selected from the group consisting of (1) a nuclear polyhedrosis virus (NPV) of *Lymantria dispar* NPV, *Anagrapha falcifera* NPV, *Spodoptera littoralis* NPV, *Mamestra brassicae* NPV, *Choristoneura fumiferana* NPV, *Trichoplusia ni* NPV, *Helicoverpa zea* NPV, *Rachiplusia ou* NPV, an *Autographa californica* NPV selected from the group consisting of V8v EGTDEL, V8vEGTDEL-AaIT, AcMNPV E2, AcMNPV L1, AcMNPV V8, AcMNPV Px1, and mixtures thereof; and (2) a granulosis virus (GV) of *Cydia pomonella* GV, *Pieris brassicae* GV, *Trichoplusia ni* GV, *Artogeia rapae* GV, *Plodia interpunctella* GV, and mixtures thereof.

34. A process as described in claim 28, wherein the DNA virus is a double stranded nonenveloped DNA virus.

35. A process as described in claim 28, wherein the DNA virus is a single stranded nonenveloped DNA virus.

36. A process as described in claim 27, wherein the viral pathogen is a RNA virus selected from the group consisting of a double stranded enveloped RNA virus, a double stranded nonenveloped RNA virus, a single stranded RNA virus, and mixtures thereof.

37. A process as described in claim 36, wherein the RNA virus is a double stranded enveloped RNA virus selected from the group consisting of Togaviridae, Bunyaviridae, Flaviviridae, and mixtures thereof.

38. A process as described in claim 36, wherein the RNA virus is a double stranded nonenveloped RNA virus selected from the group consisting of Reoviridae, Birnaviridae, and mixtures thereof.

39. A process as described in claim 36, wherein the RNA virus is a single stranded nonenveloped RNA virus selected from the group consisting of Picornaviridae, Tetraviridae, Nodaviridae, and mixtures thereof.

40. A process as described in claim 1, wherein (a) the plasticizer is selected from the group consisting of a poly(ethylene glycol), a poly(propylene glycol), a citric acid ester, diethyl phthalate, dibutyl phthalate, castor oil, triacetin, and mixtures thereof;

(b) the ultraviolet protector is selected from the group consisting of carbon black, a benzophenone, a dye, titanium dioxide, and mixtures thereof;

(c) the activity enhancer is a stilbene compound and;

(d) the glidant is selected from the group consisting of talc, magnesium stearate, calcium stearate, calcium sulfate, and mixtures thereof.

41. A process as described in claim 40, wherein (a) the polymer is selected from the group consisting of an ethyl acrylate/methacrylic acid copolymer having free carboxylic acid groups and ester groups in a ratio of about 1:1, a methyl methacrylate/methacrylic acid copolymer having free carboxylic acid groups and ester groups in a ratio of from about 1:1 to about 1:2, a methacrylic acid/methyl acrylate/methyl methacrylate copolymer having monomers in a ratio of from about 1:5:2 to about 3:7:3, and mixtures thereof;

(b) The plasticizer is selected from the group consisting of triethyl citrate and a poly(ethylene glycol) having an average molecular weight of about 1,000 to 10,000; and (c) the stilbene compound is selected from the group consisting of Blancophor BBH, Calcofluor White M2R, Phorwite AR, and mixtures thereof.

42. A process as described in claim 1, wherein the polymer is a methyl methacrylate/methacrylic acid copolymer.

43. A process as described in claim 1, wherein the mixture is spray dried.

44. A process as described in claim 1, wherein the coated pesticidal matrix has a particle size of less than about 20 μm.

45. A process as described in claim 20, wherein the coated pesticidal matrix has a particle size of from about 2 μm to 10 μm.

46. A process as described in claim 1, wherein the coated matrix comprises, on a percentage-weight-basis of the matrix, from about 1% to about 50% of the pesticidal agent, from about 5% to about 50% of the polymer, from about 0% to about 25% of the plasticizer, from about 0% to about 30% of the ultraviolet protector, from about 0% to about 75% of the activity enhancer, and from about 0% to about 15% of the glidant.

47. A coated pesticidal matrix produced by a process as described in claim 1.

48. A process for improving the residual control of a pest comprising applying to the locus of the pest a pesticidally-effective amount of a coated pesticidal matrix as described in claim 47.

49. The coated pesticidal matrix of claim 47 which includes on a percentage-weight-basis of the coated matrix, from about 1% to about 50% of said pesticidal agent, from about 5% to about 50% of said pH-dependent polymer, from about 0% to about 25% of a plasticizer, from about 0% to about 30% of an ultraviolet protector, from about 0% to about 75% of an activity enhancer, and from about 0% to about 15% of a glidant.

50. A coated pesticidal matrix as described in claim 49, wherein the coated matrix comprises, on a percentage-weight-basis of the coated matrix, from about 5% to about 35% of the pesticidal agent, from about 10% to about 45% of the polymer, from about 0% to about 25% of the plasticizer, from about 0% to about 20% of the ultraviolet protector, from about 0% to about 45% of the activity enhancer, and from about 0% to about 10% of the glidant.

51. A coated pesticidal matrix as described in claim 49, wherein (a) the plasticizer is selected from the group consisting of a poly(ethylene glycol), a poly(propylene glycol), a citric acid ester, diethyl phthalate, dibutyl phthalate, castor oil, triacetin, and mixtures thereof;

(b) the ultraviolet protector is selected from the group consisting of carbon black, a benzophenone, a dye, titanium dioxide, and mixtures thereof;

(c) the activity enhancer is a stilbene compound; and (d) the glidant is selected from the group consisting of talc, magnesium stearate, calcium stearate, calcium sulfate, and mixtures thereof.

52. A coated pesticidal matrix as described in claim 51, wherein (a) the polymer is selected from the group consisting of an ethyl acrylate/methacrylic acid copolymer having free carboxylic acid groups and ester groups in a ratio of about 1:1, a methyl methacrylate/methacrylic acid copolymer having free carboxylic acid groups and ester groups in a ratio of from about 1:1 to about 1:2, a methacrylic acid/methyl acrylate/methyl methacrylate copolymer having monomers in a ratio of from about 1:5:2 to about 3:7:3, and mixtures thereof;

(b) the plasticizer is selected from the group consisting of triethyl citrate and a poly(ethylene glycol) having an average molecular weight of about 1,000 to 10,000; and (c) the stilbene compound is selected from the group consisting of Blacophor BBH, Calcofluor White M2R, Phorwite AR, and mixtures thereof.

53. A pesticidal matrix as described in claim 49, wherein the pesticidal agent is selected from the group consisting of an insecticide, an acaricide, a nematicide, a fungicide, an herbicide, and mixtures thereof.

54. A pesticidal matrix as described in claim 53, wherein the pesticidal agent is an insecticide selected from the group consisting of a chemical insecticide, a biological insecticide, and mixtures thereof.

55. A coated pesticidal matrix as described in claim 54, wherein the insecticide is a biological insecticide selected from the group consisting of a viral pathogen, a bacterial pathogen, a fungal pathogen, and mixtures thereof.

56. A coated pesticidal matrix as described in claim 55, wherein (a) the biological insecticide is selected from the group consisting of (1) *Melolontha melolontha* EPV, *Amsacata moorei* EPB, *Locusta migratoria* EPV, *Melanoplus sanguinipes* EPV, *Schistocerca gregaria* EPV, *Aedes aegypti* EPV, *Chironomus luridus* EPV, and mixtures thereof;

(2) *Lymantria dispar* NPV, *Anagrapha falcifera* NPV, *Spodoptera littoralis* NPV, *Mamestra brassicae* NPV, *Choristoneura fumiferana* NPV, *Trichoplusia ni* NPV, *Heliocoverpa zea* NPV, *Rachiplusia ou* NPV, an *Autographa californica* NPV selected from the group consisting of V8vEFTDEL, V8vEGTDEL-AaIT, AcMNPV E2, AcMNPV L1, AcMNPV V8 and AcMNPVPx1, and mixtures thereof;

(3) *Cydia pomonella* GV, *Pieris brassicase* GV, *Trichoplusia ni* GV, *Artogeia rapae* GV, *Plodia interpunctella* GV, and mixtures thereof;

(4) Togaviridae, Bunyaviridae, Flaviviridae, and mixtures thereof;

(5) Reoviridae, Birnaviridae, and mixtures thereof;

(6) Picornaviridae, Tetraviridae, Nodaviridae, and mixtures thereof;

(7) *Bicillus thuringiensis, Bacillus lentimorbus, Bacillus cereus, Bacillus popilliae, Photorhabdus luminescens, Xeorhabdus nematophilus*, and mixtures thereof; and (8) *Beauveria bassiana*, Entomophthora spp., *Metarrhizium anisopliae,* and mixtures thereof.

57. A process for preparing a coated pesticidal matrix which includes a pesticidal agent which itself is substantially inactivated by ultra-violet radiation, but which when included in said coated matrix retains a significant amount of its original pesticidal activity, which process consists essentially of (a) preparing an aqueous mixture containing said pesticidal agent, a pH-dependent polymer, a base, optionally a plasticizer, optionally an ultraviolet protector, optionally an activity enhancer, optionally a glidant, and water;

wherein (A) said pH dependent polymer is selected from the group consisting of an ethyl acrylate/methacrylic acid copolymer having free carboxylic acid groups and ester groups in a ratio of from about 1:1 to about 1:2, a methacrylic acid/methyl acrylate/methyl methacrylate copolymer having monomers in a ratio of from about 1:5:2 to about 3:7:3, and mixtures thereof;

(B) the plasticizer is selected from the group consisting of triethyl citrate and a poly(ethylene glycol) having an average molecular weight of about 1,000 to 10,000;

(C) the activity enhancer is selected from the group consisting of Blancophor BBH, Calcofluor White M2R, Phorwite AR, and mixtures thereof;

(D) the pesticidal agent is a biological insecticide selected from the group consisting of (1) *Melolontha melolontha* EPV, *Amsacta moorei* EPB, *Locusta migratoria* EPV, *Melanoplus sanguinipes* EPV, *Schistocerca gregaria* EPV, *Aedes aegypti* EPV, *Chironomus luridus* EPV, and mixtures thereof;

(2) *Lymantria dispar* NPV, *Anagrapha falcifera* NPV, *Spodoptera littoralis* NPV, *Mamestra brassicae* NPV, *Choristoneura fumiferana* NPV, *Trichoplusia ni* NPV, *Heliocoverpa zea* NPV, *Rachiplusia ou* NPV, an *Autographa californica* NPV selected from the group consisting of V8vEFTDEL, V8vEGTDEL-AaIT, AcMNPV E2, AcMNPV L1, AcMNPV V8 and AcM NPVPx1, and mixtures thereof;

(3) *Cydia pomonella* GV, *Pieris brassicae* GV, *Trichoplusia ni* GV,*Artogeia rapae* GV, *Plodia interpunctella* GV, and mixtures thereof;

(4) Togaviridae, Bunyaviridae, Flaviviridae, and mixtures thereof;

(5) Reoviridae, Birnaviridae, and mixtures thereof, (6) Picornaviridae, Tetraviridae, Nodaviridae, and mixtures thereof;

(7) *Bacillus thuringiensis, Bacillus lentimorbus, Bacillus cereus, Bacillus popilliae, Photorhabdus luminescens, Xeorhabdus nematophilus*, and mixtures thereof; and (8) *Beauveria bassiana*, Entomophthora spp., *Metarrhizium anisopliae*, and mixtures thereof;

wherein the amount of base added is below the amount required to fully solubilize the copolymer such that no more than 10% of the free carboxylic acid groups of the copolymer are converted to salts; and wherein the mixture's pH is less than the polymer's solubilization pH; and drying the mixture to produce a coated pesticidal matrix.

58. A coated pesticidal matrix prepared according to the process of claim 57, comprising, on a percentage-by-weight basis of the coated pesticidal matrix, from about 1% to about 50% of a pesticidal agent, from about 5% to about 50% of a pH-dependent polymer, from about 0% to about 25% of a plasticizer, from about 0% to about 30% of a ultraviolet protector, from about 0% to about 75% of a activity enhancer, and from about 0% to about 15% of a glidant.

* * * * *